Figure 1:
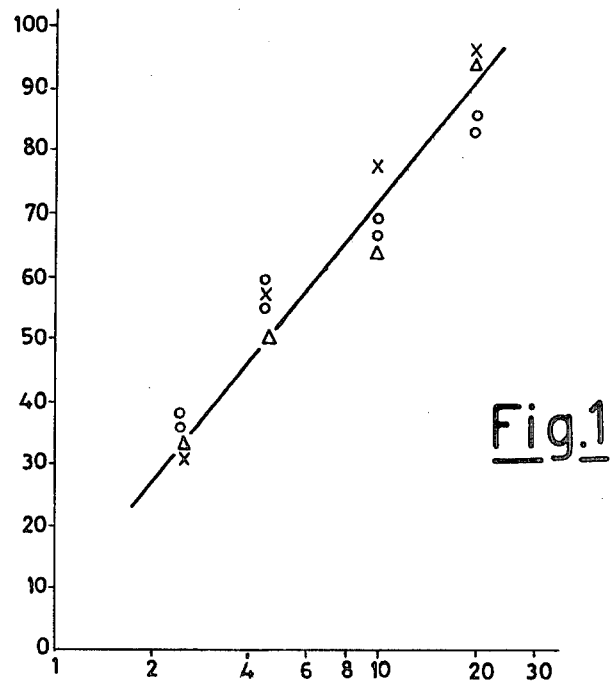

United States Patent [19]

Meiattini et al.

[11] 4,220,714
[45] Sep. 2, 1980

[54] COMPOSITION FOR INHIBITING ADENYLATE-KINASE AND ITS USE

[75] Inventors: Franco Meiattini, Siena; Giuliano Giannini; Paolo Tarli, both of Monteriggionia, all of Italy

[73] Assignee: Istituto Sieroterapico e Vaccinogeno Toscano Sclavo S.p.A., Siena, Italy

[21] Appl. No.: 896,201

[22] Filed: Apr. 13, 1978

[30] Foreign Application Priority Data

Sep. 30, 1977 [IT] Italy .................... 28139 A/77

[51] Int. Cl.$^2$ .................... C12Q 1/50; C12N 9/99
[52] U.S. Cl. .................... 435/17; 435/26; 435/184
[58] Field of Search .................... 195/99, 103.5 R, 62, 195/66 R; 252/408 R; 438/17, 15, 26, 184

[56] References Cited

U.S. PATENT DOCUMENTS 4,042,462  8/1977  Johnson et al. ............... 195/103.5 R

OTHER PUBLICATIONS

Rosano, et al., "Evaluation of Adenosine 5'-Monophosphate and Fluoride as Adenylate Kinase Inhibitors in the Creative Kinase Assay", *Chin. Chem.*, vol. 22, No. 7, pp. 1078–1083 (1976).

Szasz, et al., "Creative Kinase in Serum: 2. Interference of Adenylate Kinase with the Assay", *Clin. Chem.*, vol. 22, No. 11, pp. 1806–1811 (1976).

Szasz, et al., "Creative Kinase in Serum: 3. Further Study of Adenylate Kinase Inhibitors", *Clin. Chem.*, vol. 23, No. 10, pp. 1888–1892 (1977).

Wilkinson, *The Principles and Practice of Diagnostic Enzymology*, Year Book Medical Publishers, Inc., Chicago (1976), pp. 96–103.

*Primary Examiner*—Thomas G. Wiseman
*Attorney, Agent, or Firm*—Morgan, Finnegan, Pine, Foley & Lee

[57] ABSTRACT

A method and a combination of reagents are disclosed for determining the creatine kinase activity by inhibiting the action of creatine kinase, the improvement consisting in that adenosine - 5'- monophosphate is used in combination with an inorganic, preferably an alkali metal, fluoride. By so doing the masking effect of adenylate kinase are efficiently offset.

5 Claims, 6 Drawing Figures

COMPOSITION FOR INHIBITING ADENYLATE-KINASE AND ITS USE

This invention relates to a composition which is adapted to inhibit adenylate-kinase, especially for determining the creatinekinase activity. The invention also relates to the use of such a composition in the method for determining activity of the creatinekinase activity.

It has been long since ascertained that it is useful to determine at the creatinekinase activity in the early diagnosis of the myocardial infarct and in the progressive muscular dystrophy (J. Biochem. 46, 103, (1959); Rev. franc. Etud. Clin. Biol., 5, 386, (1960). The fundamental method, as used today, is the method described by Oliver (Biochem. J., 61, 116 (1955), which is based on the reaction catalyzed by the creatinekinase (CK) enzyme in the direction which is the most favoured from the thermodynamical standpoint. The reaction in question is summarized by the following pattern:

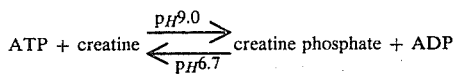

wherein ATP stands for adenosine triphosphate and ADP stands for adenosine diphosphate, coupled with side reaction which are conducive to the formation of substances susceptible of being photometrically measured:

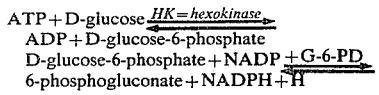

wherein G-6-PD is glucose-6-phosphate dehydrogenase, and NADPH is nicotinamide adenine dinucleotide phosphate. A considerable drawback of the above indicated method is the fact that the system referred to above is influenced by the activity of the adenylate kinase enzyme (AK) which is always present in normal sera and especially in haemolyzed samples, which catalyzes the formation of ATP according to the following pattern:

wherein AMP is adenosine-5'-monophosphate. Thus, the presence of the AK enzyme causes a visible increase of the creatine kinase (CK) activity.

Oliver himself has observed that the AK could have been inhibited by adenosine-5'-monophosphate (AMP) at concentration which were from 5 to 10 times higher than that of ADP. At any rate, at such levels, the AMP slightly inhibits also the activity of the CK and this effect is far from being negligible. Modifications have been suggested subsequently, by using AMP at lower concentrations so as not to inhibit CK appreciably while concurrently bringing about an adequate but incomplete inhibition of AK.

This problem has been dealt with also by other authors and other methods have been suggested for reducing the influence of the AK activity. For example, it has been suggested to use AMP and diadenosine pentaphosphate (Clin. Chem., 22, 1078 (1976)) or fluoride (Clin. Chem., 22, 1806 (1976)). However diadenosine pentaphosphate plus AMP does not cause a sufficient inhibition of AK of hepatic origin, whereas the fluoride, at the concentration which is required to inhibit AK, may cause the precipitation of magnesium (which must be added to the system as an activator) in the form of $MgF_2$. We have found, that which is the subject matter of the present invention, that it is possible to effect the determination of the creatine kinase activity without the drawbacks referred to above by employing a composition, which also belongs to the present invention, composed by AMP and a fluoride, employed simultaneously at low concentrations. By so doing the disturbing action of AK is reduced to a negligible level without any significant loss of the creatine kinase activity and without causing any precipitation of $MgF_2$. The composition just now suggested contains the two reagents in proportions which are variable from 1:0.15 to 1:25 and its action has been checked by adding the reagent in proportions variable from 1:30 to 1:60 (volume ratio, serum-reagent).

We have thus ascertained that the simultaneous action of low concentrations of AMP and fluoride improves the performance of the system for the determination of the creatine kinase activity.

Figure 2:
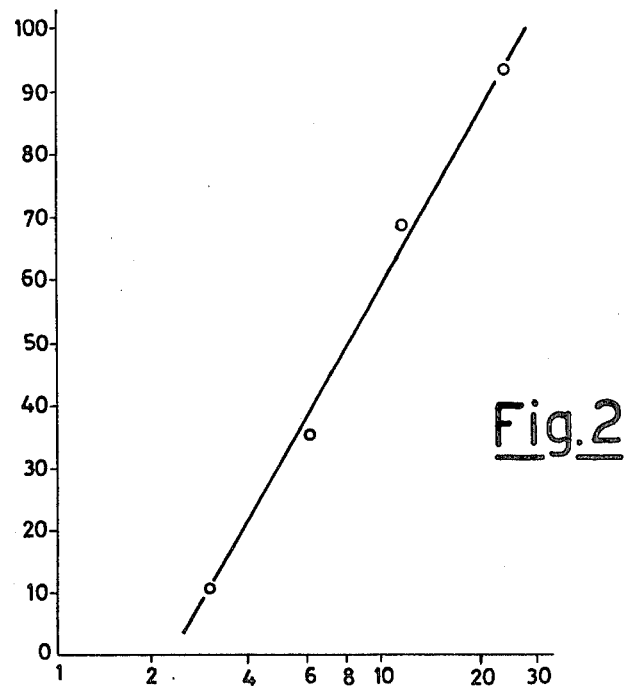
Figure 4:
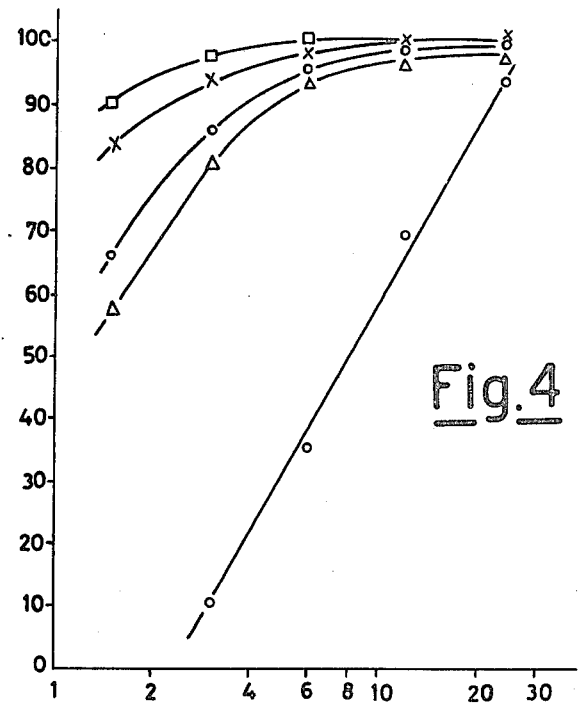

High levels of inhibition against AK can thus be achieved, preventing both the inhibition of CK and the precipitation of magnesium fluoride. As a matter of fact, we have seen that, when used together, AMP and the fluoride show a different behaviour relative to AK, as compared with that which is experienced when these two substances are used separately (FIGS. 1, 2, 4).

The inhibition of AK is extremely significant, also.

In order to be able to check the stability of the reagent as regards the precipitation of $MgF_2$, the reagent has been subjected to abrupt temperature changes: switching from the refrigerator at $+5°$ C. to the thermostat at $+37°$ C., freezing and thawing cycles and storage for 6 months continuously at $5°$ C., $20°$ C. and $37°$ C. Obviously, under such conditions, the enzymatic activity of HK and G-6-PD is destroyed the only exception being the sample stored at $5°$ C. At any rate, no precipitation of $MgF_2$ has ever been experienced.

It is to be noted, in addition, that lag phases longer than 1 minute have never been experienced when using the method and the reagent suggested hereby, that which indicates that the CK activity is not affected in any wise. With the conventional reagents, the lag phase lasts, generally, from 3 to 5 minutes.

MATERIALS AND METHODS

Creatine phosphate, ADP and AMP have been supplied by Prochifar, Milan. HK (from yest), G-6-PD (from L-mesenteroid) were supplied by PL-Biochemicals Inc., Wisconsin; N-acetylcystene, D-glucose, potassium fluoride, imidazole and acetic acid, all by the firm E. Merck, Darmstadt, Germany.

Normal and abnormal sera (from myocardial infarct) and the haemolysate from human erythrocytes were used as sources of CK and of AK.

The AK of hepatic and muscular origin was obtained from rat and rabbit liver and muscle homogenates, according to Szasz et al.

The AK activity was determined according to the method by Szasz et al. (Clin. Chem., 22, 1806, (1976)). Table I shows the concentrations of the reagents in the reaction mixture. 0.05 ml of serum were added to 3 ml of the reagent, the latter having been preheated to $37°$ C. and the reaction speed at 340 nm was recorded, so as to check the lag phase of each serum. A spectrophotometer, Beckman-25 with basin-supporting cradle and thermostat, was used. The reaction temperature for determining both AK and CK was 37° C. The statistical analysis of the results has been made by adopting the "t" test by Student (Snedecor, C. W. and Cochran W. G., Statistical Method, The Iowa State University Press, Ames, Iowa, 1968).

RESULTS

We have checked the inhibition of the AK activity and of the CK activity by AMP and the fluoride.

Figure 3:
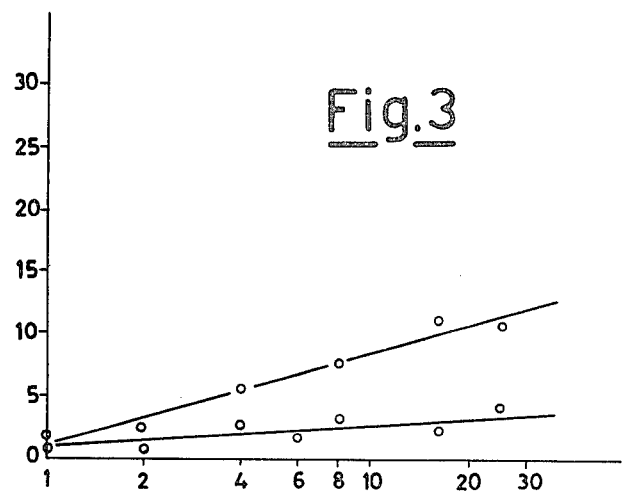

Without fluoride, the 95% of inhibition of AK was attained with more than 20 millimols per liter of AMP (FIG. 1). Without AMP, the 95% of inhibition was reached with 25 millimols per liter of fluoride (FIG. 2). Anyhow, AMP at 20 millimols per liter inhibits even more than 10% of CK activity and the fluoride at 25 millimols per liter inhibits at least the 4% of the CK activity (FIG. 3).

Figure 5:
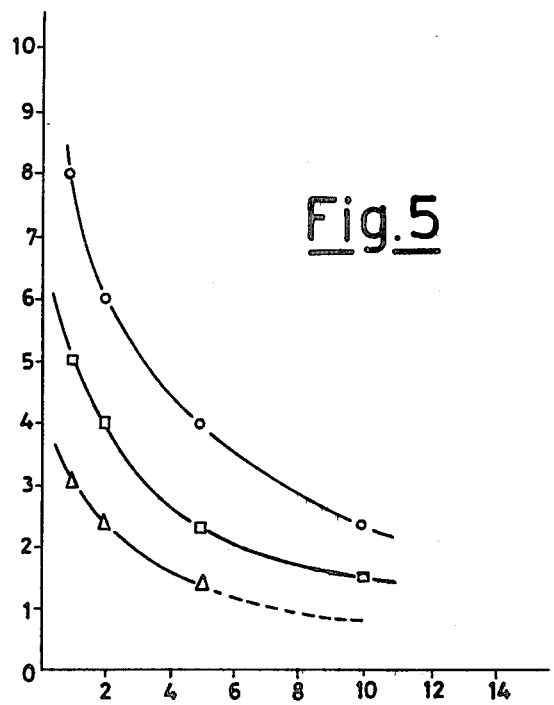

Using AMP and the fluoride together, the 95% of the AK activity was obtained with a little as 2 millimols of AMP and 6 millimols of fluoride, per liter (FIG. 4). FIG. 5 shows the admixtures of AMP and fluoride for obtaining fixed percentages of inhibition of the AK.

Figure 6:
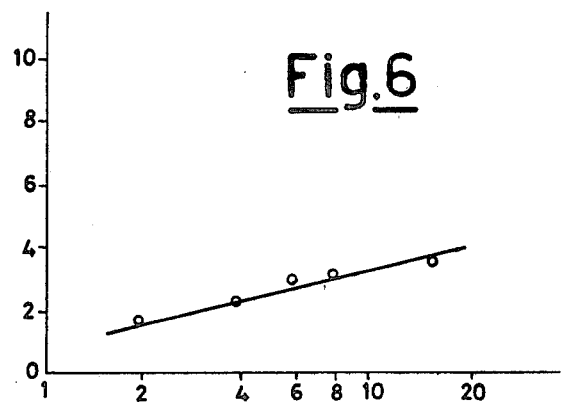

At the concentrations which are adopted, the inhibition of CK was not stronger than 3% (FIG. 6).

The method suggested herein has been checked by determining the CK activity in normal sera, without erythrocyte AK and with increasing quantities of it. Such samples have been analyzed with the method described herein and with that which uses AMP at 5 millimols per liter. No significant differences have been found between the normal samples and those having added erythrocyte AK, in the case of the method of the invention, with 2 millimols per liter of AMP and 6 millimols per liter of fluoride (P more than 0.05).

By using the method with AMP only, at 5 millimols per liter a most significant difference has been found (P less than 0.01) and values have been obtained, for the samples with erythrocyte AK, which exceeded by about 50% those of the normal samples.

We have also determined the inhibition of the AK of hepatic origin, cardiac origin and muscular origin, with AMP 2 millimols per liter plus fluoride at 6 millimols per liter. Table 2 shows the results.

The inhibition of the AK activity was always greater than 70%.

TABLE I

| COMPOSITION OF THE COMBINED REAGENT |
| --- |
| (All the concentrations refer to the final reaction mixture) |

| | |
| --- | --- |
| Imidazole acetate buffer | 100 millimol/liter |
| Creatine phosphate | 30 " |
| ADP | 2 " |
| N-acetylcysteine | 20 " |
| D-glucose | 20 " |
| Mg acetate | 10 " |
| NADP+ | 2 " |
| HK | 2,000 Units/liter |
| G-6-PD | 2,000 do. |
| pH 6.7 (at 25° C.) | |

During the experimental runs AMP and fluoride have been used at different concentrations, but the optimum values adopted as final were 2 millimols per liter of AMP and 6 millimols per liter of the fluoride.

TABLE 2

Effect of AMP 2 mmol/liter and Fluoride 6 mmol/liter on Adenylate Kinase activity from different sources

| Source of AK | Szasz method (10) AK (mU/ml) | plus AMP 2 mmol/l and fluoride 6 mmol/l* AK (mU/ml) | % inhibition |
| --- | --- | --- | --- |
| Rat liver | 864 | 205 | 76 |
| muscle | 3064 | 843 | 72 |
| heart | 1755 | 483 | 72 |
| Rabbit liver | 265 | 73 | 72 |
| muscle | 1981 | 389 | 80 |
| heart | 989 | 189 | 81 |
| Monkey liver | 1687 | 355 | 79 |
| muscle | 36335 | 6154 | 83 |
| heart | 4433 | 613 | 86 |
| Human liver | 1133 | 58 | 95 |
| muscle | 7802 | 245 | 97 |
| heart | 1275 | 49 | 96 |
| erthrocytes | 978 | 40 | 96 |
| platelets | 285 | 7 | 98 |

*The indicated concentration of AMP and the fluoride have been added to the reagent used for determining AK according to the reference method (10).

As regards the symbols used in this specification, it is confirmed that the respective meanings are:
  CK=creatine kinase (EC 2.7.3.2.) ATP: creatine phosphotransferase
  HK=hexokinase (EC 2.7.1.1.) ATP: D-hexose-6-phosphotransferase
  AK=adenylate kinase (myokinase) (EC 2.7.4.3.) ATP: AMP phosphotransferase
  G-6-PD=glucose-6-phosphate dehydrogenase (EC 1.1.1.49) D-glucose-6-phosphate-NADP+-1-oxidoreductase.

Having reference to the accompanying drawings again, the following indications are given:

FIG. 1 shows the effect of AMP on the activity of the adenylate kinase of erythrocyte origin. The ordinates report the percentage of the Ak inhibition, and the abscissae report the concentrations in millimols per liter, of AMP.

The concentrations of haemoglobin in the sample are:

| o 225 milligram/deciliter | 0 110 milligrams/ml |
| --- | --- |
| Δ50 milligrams/deciliter | x 25 milligrams/decilitre |

FIG. 2 shows the effects of the fluoride on the activity of the adenylate kinase. The ordinates report the percentage of inhibition of AK and the abscissae the concentrations, in millimols per liter, of the fluoride.

The concentration of haemoglobin in the samples is 225 milligram/deciliter.

FIG. 3 shows the effect of AMP plus fluoride on the activity of the creatine kinase from serum. Each value represent the average of five independent readings.

All the CK activities were corrected by allowing for the AK activity.

The CK activities were in the range from 196 to 1030 Units per liter. The same samples were used both for AMP and the fluoride. The ordinates report the percentage relative to the inhibition of the creatine kinase and the abscissae indicate the concentrations of AMP, or fluoride, in millimols per liter, in FIG. 3.

FIG. 4 shows the effect of AMP plus the fluoride on the activity of the adenylate kinase from erythrocytes.

Concentration of haemoglobin in the sample: 225 milligrams per deciliter.

Concentrations of AMP:

| | |
|---|---|
| o 0 millimols/liter; | Δ 1 millimol/liter |
| x 5 millimol/liter; | □ 10 millimol/liter |
| 0 2 millimol/liter; | |

The ordinates always report the percentage of inhibition of AK and the abscissae indicate the concentration of the fluoride in millimol per liter.

FIG. 5 shows the effect of AMP plus fluoride on the activity of adenylate kinase from erythrocytes. The three curves are referred:

| | |
|---|---|
| o 95% | of AK inhibition |
| □ 90% | " |
| Δ 80% | " |

The ordinates report the concentrations of fluoride in millimols/liter and the abscissae show the concentrations of AMP.

FIG. 6 shows the effect of the fluoride on the activity of the creatine kinase, with AMP at the constant concentration of 2 millimols per liter.

The ordinates report the percentage of inhibition (relative) of CK and the abscissae report the concentration of the fluoride in millimols per liter.

What is claimed is:

1. A composition for the inhibition of adenylate kinase, said composition comprising adenosine-5$^1$-monophosphate and a fluoride, at a ratio of from 1:01.5 to 1:25.

2. A composition defined in claim 1 wherein the fluoride is potassium fluoride.

3. A composition as defined in claim 1 wherein the concentration of the adenosine-5$^1$-monophosphate is 2 m moles and the fluoride concentration is 6 m moles.

4. A method for determining creatine kinase activity said method comprising adding to the sample to be tested a composition which comprises adenosine-5$^1$-monophosphate and a fluoride at a ratio of 1:01.5 to 1:25, incubating the composition-sample mixture under conditions suitable for creatine kinase activity, and thereafter spectrophotometrically measuring the creatine kinase activity.

5. A method for the determination of the creatine kinase activity according to claim 4 characterized in that the composition is added to the sample; to be tested in a proportion which varies from 1:30 to 1:60 (volume ratio of the serum to the reagent).

* * * * *

UNITED STATES PATENT AND TRADEMARK OFFICE
CERTIFICATE OF CORRECTION

PATENT NO. : 4,220,714

DATED : September 2, 1980

INVENTOR(S) : Meiattini et al.

It is certified that error appears in the above-identified patent and that said Letters Patent is hereby corrected as shown below:

In column 6, claim 1, line 7, "1:01.5" should read --1:0.15--.

In column 6, claim 4, line 17, "1:01.5" should read --1:0.15--.

Signed and Sealed this

First Day of October 1985

[SEAL]

Attest:

Attesting Officer

DONALD J. QUIGG

Commissioner of Patents and Trademarks—Designate